United States Patent [19]

Nakao et al.

[11] Patent Number: 5,153,194

[45] Date of Patent: * Oct. 6, 1992

[54] THIENOCYCLOHEPTAPYRIDAZINE COMPOUNDS AND THEIR PHARMACEUTICAL USE

[75] Inventors: Tohru Nakao, Nakatsu; Hiroshi Tanaka, Fukuoka; Yasuto Morimoto; Shuzo Takehara, both of Nakatsu, all of Japan

[73] Assignee: Yoshitomi Pharmaceutical Industries, Ltd., Osaka, Japan

[*] Notice: The portion of the term of this patent subsequent to Oct. 23, 2007 has been disclaimed.

[21] Appl. No.: 490,609

[22] PCT Filed: Sep. 20, 1989

[86] PCT No.: PCT/JP89/00956

§ 371 Date: May 17, 1990

§ 102(e) Date: May 17, 1990

[30] Foreign Application Priority Data

Sep. 21, 1988 [JP] Japan .................... 63-237600

[51] Int. Cl.$^5$ .................... C07D 495/04; A61K 31/50
[52] U.S. Cl. .................... 514/248; 544/234; 549/51
[58] Field of Search .................... 544/234; 514/248

[56] References Cited

U.S. PATENT DOCUMENTS

| | | | |
|---|---|---|---|
| 4,602,019 | 7/1986 | Sircar et al. | 514/248 |
| 4,692,447 | 9/1987 | Cignarella et al. | 544/234 |
| 4,755,511 | 7/1988 | Warrington | 544/234 |
| 4,782,057 | 11/1988 | Tahara et al. | 514/248 |
| 4,843,075 | 6/1989 | Nakao et al. | 514/248 |
| 4,849,421 | 7/1989 | Nakao et al. | 514/248 |
| 4,965,264 | 10/1990 | Nakao et al. | 544/234 |

FOREIGN PATENT DOCUMENTS

0308515A1 3/1989 European Pat. Off. .

OTHER PUBLICATIONS

J. Lombardino et al., J. Med. Chem. 1981, 24, 830–834.

Primary Examiner—Mukund J. Shah
Assistant Examiner—E. Bernhardt
Attorney, Agent, or Firm—Wenderoth, Lind & Ponack

[57] ABSTRACT

A thienocycloheptapyridazine compound of the formula ,0010 wherein R stands for hydrogen, a halogen or a $C_{1-4}$ alkyl, Ar stands for an aryl, a heteroaryl, or an aryl or a heteroaryl having as a substituent at least a halogen, a $C_{1-4}$ alkyl, a $C_{1-4}$ alkoxy, nitro, amino, hydroxy, trifluoromethyl and/or a $C_{2-5}$ alkanoylamino; and the bond ------ between 4-position and 4a-position represents a single bond or a double bond, which is useful as an antianxiety agent, amnesia-treating drug, a brain function-activating drug or an antidementiac drug.

5 Claims, No Drawings

THIENOCYCLOHEPTAPYRIDAZINE COMPOUNDS AND THEIR PHARMACEUTICAL USE

TECHNICAL FIELD

This invention relates to thienocycloheptapyridazine compounds which are novel and of use as pharmaceuticals, and to their pharmaceutical use.

BACKGROUND ART

Benzodiazepine, (BZP) ,derivatives represented by diazepam have been use for a long as an antianxiety drug or a therapeutic medicine for sleep disturbance. The recent pharmacological studies have shown that there exist receptors which exhibit a specific affinity for BZP derivatives in the central nervous system [Science, vol. 198, 849 (1977)]. In the studies and researches conducted subsequently, there have been investigated and developed not only BZP derivatives but also compounds which have structures different from BZP but exhibit a high affinity for BZP receptors and a BZP-like action (BZP agonist), compounds which exhibit a high affinity for BZP receptors but exhibit a pharmacological action the reverse of BZP (BZP inverse agonist), and compounds which exhibit a high affinity for BZP receptors but nevertheless exhibit no pharmacological activity themselves and rather show an antagonistic action against the action of the agonist or the inverse-agonist (BZP antagonist) [Advance in Drug Research, vol. 14, 165 (1985)].

Since BZP derivatives which are used as an antianxiety drug have a sedative action, a muscle-relaxing action and an anticonvulsive action in addition to an antianxiety action, they often cause troubles in terms of side effects such as dizziness and sleepiness. Thus, researches of non-BZP types of compounds aiming at developing selective antianxiety drugs with less side effects are thriving. Nevertheless, there have not been found satisfactory ones yet.

Also, in recent years, amnesia-inducing actions by BZP agonists were found [Nature, vol. 321, 864 (1986)], and there have been reports suggesting the possibility that BZP-antagonists exhibiting an antagonistic action against the amnesic actions induced by BZP agonists, and BZP-inverse-agonists exhibiting an action reverse to the amnesic actions by BZP agonists, are usable as brain-function activating drugs. [Trends in Neurosciences, vol. 11, 13 (1988)].

In the meantime, in the specification of U.S. Pat. No. 4,602,019 there are disclosed compounds such as 2,4,4a,5-tetrahydro-7 -(1H-imidazol-1-yl)-3H-indeno[1,2-c]pyridazin-3-one having a cardiac action and an antihypertensive action. The Journal of Medicinal Chemistry, vol. 24, 830 (1981) discloses compounds such as 2-(4-chlorophenyl)benzothiopyrano-[4,3-c]pyrazol-3-one possessing an immune-supressing action.

DISCLOSURE OF INVENTION

The present inventors have conducted intensive studies for the purpose of developing BZP-agonists, BZP-inverse-agonists or BZP-antagonists having a non-BZP-nucleus which are useful pharmaceuticals, and providing effective compounds and pharmaceuticals.

It has been found that the above-mentioned purpose can be attained according to the present invention described hereinafter.

That is, the first invention is to provide thienocycloheptapyridazine compounds of the formula

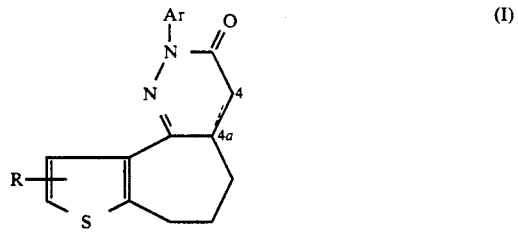

wherein R stands for hydrogen, a halogen or a $C_{1-4}$ alkyl, Ar stands for an aryl, a heteroaryl, or an aryl or a heteroaryl having as a substituent at least a halogen, a $C_{1-4}$ alkyl, a $C_{1-4}$ alkoxy, nitro, amino, hydroxy, trifluoromethyl and/or a $C_{2-5}$ alkanoylamino; and the bond ----------- between 4-position and 4a-position represents a single bond or a double bond.

The second invention is to provide pharmaceutical compositions comprising a thienocycloheptapyridazine compound of the above formula (I).

The symbols of the formula (I) and each of the below-mentioned formulae are defined in detail below. The halogen represents chlorine, bromine, fluorine or the like; the $C_{1-4}$ alkyl represents methyl, ethyl, propyl, isopropyl, butyl, isobutyl or tert-butyl; the $C_{1-4}$ alkoxy represents methoxy, ethoxy, propoxy, isopropoxy, butoxy, isobutoxy or tert-butoxy; the $C_{2-5}$ alkanoylamino represents acetylamino, propionylamino, butyrylamino or pivaloylamino; the aryl represents phenyl, naphthyl or the like; and the heteroaryl represents a 5- or 6-membered ring or its fused ring containing 1 to 3 (preferably 1 or 2) hetero atom(s) (e.g. nitrogen, oxygen, sulfur) on the ring such as 2-, 3-, or 4-pyridyl, 2- or 3-thienyl, 3- or 4-pyrazolyl, 1- or 2-imidazolyl, 2-, 4- or 5-pyrimidinyl, 3-, 4- or 5-pyridazinyl or 2-, 4- or 5-benzimidazolyl.

Preferable compounds of the present invention are the compounds selected from the group consisting of 2-(4-chlorophenyl)-9-methyl-2,4,4a,5,6,7-hexahydro-3H-thieno[2',3':6,7]cyclohepta[1,2-c]pyridazin-3-one, 2-(4-methylphenyl)-9-methyl-2,4,4a,5,6,7-hexahydro-3H-thieno[2',3':6,7]cyclohepta[1,2-c]pyridazin-3-one, 2-phenyl-9-methyl-2,4,4a,5,6,7-hexahydro-3H-thieno[2',3':6,7]cyclohepta[1,2-c]pyridazin-3-one, 2-(4-methoxyphenyl)-9-methyl-2,4,4a,5,6,7-hexahydro-3H-thieno[2',3':6,7]cyclohepta[1,2-c]pyridizin-3-one, 2-(4-chlorophenyl)-2,5,6,7-tetrahydro-9-methyl-3H-thieno[2',3':6,7]cyclohepta[1,2-c]pyridazin-3-one, 2-(4-chlorophenyl)-2,4,4a,5,6,7-hexahydro-3H-thieno[2',3':6,7]cyclohepta[1,2-c]pyridizin-3-one, 2-(6-chloro-2-pyridyl)-2,4,4a,5,6,7-hexahydro-3H-thieno]2',3':6,7]cyclohepta[1,2-c]pyridazin-3-one, 2-(4-methylphenyl)-2,4,4a,5,6,7-hexahydro-3H-thieno[2',3':6,7]cyclohepta[1,2-c]pyridazin-3-one, 2-(4-methoxyphenyl)-2,4,4a-5,6,7-hexahydro-3-H-thieno[2',3':6,7]cyclohepta-[1,2-c]pyridazin-3-one, 9-bromo-2-(4-chlorophenyl)-2,4,4a,5,6,7-hexahydro-3H-thieno[2',3':6,7]cyclohepta[1,2-c]pyridazin-3-one, 9-bromo-2-(4-methoxyphenyl)-2,4,4a,5,6,7-hexahydro-3H-thieno[2',3':6,7]cyclohepta[1,2-c]pyridazin-3-one and 9-bromo-2-(4-chlorophenyl)-2,5,6,7-tetrahydro-3H-thieno[2',3':6,7]cyclohepta[1,2-c]pyridazin-3-one.

The compounds of the formula (I) can be produced by subjecting to ring-closure reaction a compound of the formula

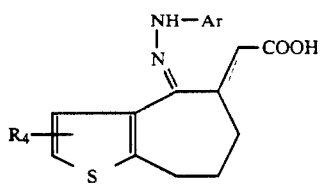

wherein each of the symbols is as defined above, which can be obtained by reacting a compound of the formula

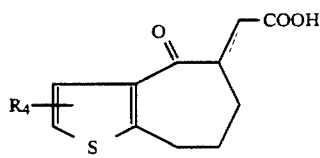

wherein R is as defined above, with a hydrazine derivative of the formula

wherein Ar is defined as above or its acid addition salt.

The reactions proceed by heating under reflux in a suitable solvent, for example, an alcohol solvent such as methanol, ethanol or propanol, or inert solvent such as benzene or toluene for 5 to 20 hours to yield the compound of the formula (I) and the compound of the formula (IV).

In case where an acid addition salt of the hydrazine derivative of the formula (III) is employed, the reaction is conducted in the presence of an acid scavenger (sodium acetate, potassium acetate, sodium bicarbonate, sodium carbonate, potassium carbonate, pyridine, triethylamine, etc.).

When the compound of the formula (IV) is obtained in the above reaction, the compound of the formula (I) can be produced by heating the obtained compound of the formula (IV) under reflux in acetic acid for 5-10 hours.

The compound of the formula (I) wherein the bond between 4-position and 4a-position is a double bond can be synthesized also by adding bromine in an amount of 1-1.5 times mol dropwise to the corresponding compound of the formula (I) wherein the bond between 4-position and 4a-position is a single bond, in acetic acid as the solvent at 20°-60° C. [Journal of Medicinal Chemistry, vol. 14, 262 (1971)], or by reacting the compound of the formula (I) wherein the bond between 4-position and 4a-position is a single bond with sodium-m-nitrobenzenesulfonate (Bachmann method, The specification of United Kingdom Patent No. 1168291).

The compounds of the formula (I) which can be produced in the above-mentioned manner can be isolated and purified by a conventional method such as column chromatography or recrystallization.

The compounds of the formula (II) of this invention are novel compounds which have not been described in any literature. The compounds can be produced by, for example, converting the corresponding compounds of the formula

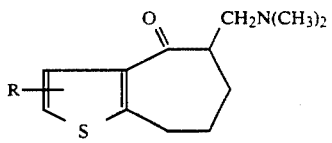

wherein R is as defined above, or their acid addition salts to their quaternary ammonium compounds by adding methyl iodide to the compounds of the formula (V) or their acid addition salts in acetone and retaining the mixture at room temperature for 2-5 hours, followed by converting the quaternary ammonium compounds to the corresponding cyano compounds of the formula

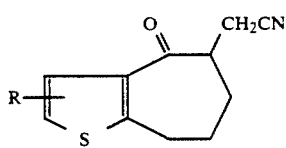

wherein R is as defined above, by adding potassium cyanide or sodium cyanide to the quaternary ammonium compounds in an aqueous methanol and reacting the mixture at 30°-50° C. for 4-10 hours, followed by adding the thus-obtained compounds of the formula (VI) to acetic acid and conc. hydrochloric acid and heating the mixture reflux under for 5-12 hours.

For reference sake, representative examples of the compounds of the formula (II) are indicated with their physical constant below.

2-Methyl-4-oxo-5,6,7,8-tetrahydro-4H-cyclohepta[b]-thiophene-5-acetic acid, melting at 155.5°-157.5° C.

4-Oxo-5,6,7,8-tetrahydro-4H-cyclohepta[b]thiophene-5-acetic acid, melting at 130°-131° C.

2-Bromo-4-oxo-5,6,7,8-tetrahydro 4H-cyclohepta[b]-thiophene-5-acetic acid, melting at 129°-131° C.

The compounds of the formula (I) exhibit a high affinity of $10^{-8}$-$10^{-9}$M to BZP receptors and have an antagonistic action against chemical convulsants such as bicuculline and pentylenetetrazole. They also exhibit an inhibitory action against amnesia induced by electroconvulsive shock.

The pharmacological actions of the compounds of the present invention are shown with the experimental methods therefor below.

EXPERIMENTAL EXAMPLE 1: DISPLACEMENT ABILITY FOR BENZODIAZEPINE

The experiment for specific affinity to benzodiazepine receptors was carried out in accordance with the method described in Life Science, vol. 20, 2101 (1977).

The crude cynaptosome fraction was isolated from the cerebral cortex of male Wistar rats aged 9-10 weeks, and was suspended in 50 mM Tris-hydrochloric acid buffer solution (pH 7.4) containing 120 mM sodium chloride and 5 mM potassium chloride. These suspensions were used for the experiment.

The test compounds in several different concentrations and tritiated diazepam (in final concentration of 2 nM) were added to the synaptosome suspensions, and the mixtures were incubated at 0° C. for 20 minutes. These suspensions were filtered with Whatman GF/B glassfiber filters. After the filters were washed with the above-mentioned buffer solution, the radioactivity left on the filters was measured with the use of a liquid scintillation counter.

Specific binding was determined by subtracting binding in the presence of $10^{-6}$M unlabelled diazepam from total binding.

According to the foregoing experimental method, the binding force to benzodiazepine receptors of the compound of the present invention is evaluated from its displacement ability for tritiated diazepam at its binding site, which is represented by Ki value (nM).

The results of the experiment are shown in Table 1.

TABLE 1

| Test compound (Example No.) | Affinity to BZP Receptors, Ki (nM) |
| --- | --- |
| 1 | 4.8 |
| 4 | 1.1 |

EXPERIMENTAL EXAMPLE 2 : ANTI-BICUCULLINE ACTION

The anti-bicuculline action test was carried out in accordance with the method described in Life Science, vol. 21, 1779 (1977).

Male ddY mice weighing 20-28 g, 7-14 animals per group, were used. One hour after the oral administration of the test compounds, (+) bicuculline was intravenously administered at the dosage of 0.6 mg/kg, and 50% effective concentration ($ED_{50}$) was estimated by examining whether tonic convulsion within 5 minutes was caused or not. The result was that the $ED_{50}$ values of the compounds of Example 1 and 5 were 8.1 mg/kg and 9.8 mg/kg, respectively.

EXPERIMENTAL EXAMPLE 3 : ACTION ON EXPERIMENTAL AMNESIA

Twenty male ddY mice were used per group to investigate the action of the test compounds on learning and memory ability of amnesia-induced mice by observing a step-through passive avoidance reflex. Amnesia-induced animals were prepared by applying electroconvulsive shock (ECS) soon after the acquisition trial and the retention test was carried out 24 hours after the acquisition trial. Test compounds were administered intraperitoneally (i.p.) 30 minutes before the acquisition trial.

As the result, it was found that the compound of Example 4 significantly prolonged the latency time in the trial of the retention test at the dose of 2.5 mg/kg (i.p.) or more and exhibited an improvement action on amnesia.

EXPERIMENTAL EXAMPLE 4 : ACUTE TOXICITY

Five male ddY mice were used per group. The mice were administered with 300 mg/kg of the compound of Example 4 intraperitoneally, but all mice survived for 5 days after the administration. Similarly, the mice were orally administered with 1000 mg/kg of the compound, but they survived for 5 days after the administration.

As apparent from the foregoing various pharmacological studies including experiments, the compounds (I) of the present invention have a high affinity for BZP receptors and exhibit an antagonistic action against chemical convulsion-inducing agents such as bicuculline and pentylenetetrazole, whereas they influence to a small extent somatic functions such as muscle relaxing actions. Thus, they are useful as an antianxiety agent. Also, since they possess an inhibitory action on amnesia induced by electroconvulsive shock, they are useful as an amnesia-treating drugs, brain function-activating drugs and antidementiac drugs. They are also of value as an antidote for excessive administration of or toxicosis by existent antianxiety drugs such as diazepam.

When the compounds of the formula (I) are used as pharmaceuticals, a therapeutically effective amount of the compounds and adequate pharmacologically acceptable additives such as excipient, carrier, diluent and so on are mixed to be formulated into a form such as tablets, capsules, granules, syrups, injectable solutions, suppositories, dispersible powders or the like and are administered in a form mentioned above. The dosage, for example, in the case of oral administration, is generally about 5-500 mg daily per adult, which is administered once a day or in divided doses several times a day.

Below, this invention is more specifically described with working examples, which are not to be construed as limitative.

EXAMPLE 1

A suspension of 2.5 g of 2-methyl-4-oxo-5,6,7,8-tetrahydro-4H-cyclohepta[b]thiophene-5-acetic acid and 1.95 g of 4-chlorophenyl hydrazine in 50 ml of toluene is refluxed under heating for 4 hours. After cooling, the mixture is concentrated under reduced pressure and the precipitated crystals are recrystallzed from ethanol to give 2.7 g of 2-(4-chlorophenyl)-9-methyl-2,4,4a,5,6,7-hexahydro-3H-thieno[2',3':6,7]cyclohepta[1,2-c]pyridazin-3-one, melting at 119°-121° C.

EXAMPLE 2

The reaction and procedure are conducted in the same manner as in Example 1 using 4-methylhydrazine in place of 4-chlorophenylhydrazine as used in Example 1 to give 2-(4-methylphenyl)-9-methyl-2,4,4a,5,6,7-hexahydro-3H-thieno[2',3':6,7]cyclohepta[1,2-c]pyridazin-3-one, melting at 117°-119° C.

EXAMPLE 3

The reaction and procedure are conducted by the same method as of Example 1 using phenylhydrazine instead of 4-chlorophenylhydrazine as used in Example 1 to give 2-phenyl-9-methyl-2,4,4a,5,6,7-hexahydro-3H-thieno[2',3':6,7]cyclohepta[1,2-c]pyridazin-3-one, melting at 102°-103° C.

EXAMPLE 4

The reaction and procedure are conducted by the same method as of Example 1 using 4-methoxyphenylhydrazine in place of 4-chlorophenylhydrazine as used in Example 1 to give 2-(4-methoxyphenyl)-9-methyl-2,4,4a,5,6,7-hexahydro-3H-thieno[2',3':6,7]cyclohepta[1,2-c]pyridazin-3-one, melting at 136°-138.5° C.

EXAMPLE 5

To a solution of 3.6 g of 2-(4-chlorophenyl)-9-methyl-2,4,4a,5,6,7-hexahydro-3H-thieno[2',3':6,7]cyclohepta[1,2-c]pyridazin-3-one in 30 ml of acetic acid is added 0.6 ml of bromine at 40° C. with stirring and the reaction mixture is stirred at 40-45° C. for 30 minutes. The mixture is poured into water and the resultant oil is collected by decantation. The crude product is subjected to column chromatography on silica gel and eluted with chloroform to give 1.27 g of 2-(4-chlorophenyl)-2,5,6,7-tetrahydro-9-methyl-3H-thieno[2',3':6,7]cyclohepta[1,2-c]pyridazin-3-one, melting at 149.5°-151° C.

EXAMPLE 6

A suspension of 2.0 g of 4-oxo-5,6,7,8-tetrahydro-4H-cyclohepta[b]thiophene-5-acetic acid and 1.6 g of 4-chlorophenylhydrazine in 40 ml of ethanol is refluxed under heating for 8 hours. After cooling, the mixture is concentrated under reduced pressure and the ethanol is distilled off. The residue is dissolved in 40 ml of acetic acid and the solution is refluxed under heating for 2 hours. After distilling off the acetic acid under reduced pressure, the resultant residue is subjected to column chromatography on silica gel. The crystals obtained from the fraction which has been eluted with chloroform are recrystallized from a mixed solvent of chloroform and ethanol to give 2.0 g of 2-(4-chlorophenyl)-2,4,4a,5,6,7-hexahydro-3H-thieno[2',3':6,7]cyclohepta[1,2-c]pyridazin-3-one as pale brown crystals, melting at 156°-158° C.

The following compounds can be obtained in the same manner as in the above examples.

EXAMPLE 7

2-(6-Chloro-2-pyridyl)-2,4,4a,5,6,7-hexahydro-3H-thieno[2',3':6,7]cyclohepta[1,2-c]pyridazin-3-one, melting at 165°-167° C.

EXAMPLE 8

2-(4-Methylphenyl)-2,4,4a,5,6,7-hexahydro-3H-thieno[2',3':6,7]cyclohepta[1,2-c]pyridazin-3-one, melting at 105°-107° C.

EXAMPLE 9

2-(4-Methoxyphenyl)-2,4,4a,5,6,7-hexahydro-3H-thieno[2',3':6,7]cyclohepta[1,2-c]pyridazin-3-one, melting at 135°-137° C.

EXAMPLE 10

9-Bromo-2-(4-chlorophenyl)-2,4,4a,5,6,7-hexahydro-3H-thieno[2',3':6,7]cyclohepta[1,2-c]pyridazin-3-one, melting at 129°-131° C.

EXAMPLE 11

9-Bromo-2-(4-methoxyphenyl)-2,4,4a,5,6,7-hexahydro-3H-thieno[2',3':6,7]cyclohepta[1,2-c]pyridazin-3-one, melting at 139°-141° C.

EXAMPLE 12

To a solution of 2.5 g of 9-bromo-2-(4-chlorophenyl)-2,4,4a,5,6,7-hexahydro-3H-thieno[2',3':6,7]cyclohepta[1,2-c]pyridazin-3-one in 40 ml of acetic acid is added a solution of 1.1 g of bromine in 5 ml of acetic acid with stirring at 40° C. over a period of 10 minutes. The mixture is stirred at 40°-50° C. for 20 minutes and poured into ice-cold water. The precipitated crystals are collected by filtration, washed with water, dissolved in chloroform and subjected to column chromatography on silica gel. The crystals obtained from the fraction which has been eluted with chloroform are recrystallized from a mixed solvent of ethanol and chloroform to give 1.5 g of 9-bromo-2-(4-chlorophenyl)-2,5,6,7-tetrahydro-3H-thieno[2',3':6,7]cyclohepta[1,2-c]pyridazin-3-one as white crystals, melting at 143°-144° C.

The compounds shown in the following tables can be obtained in the same manner as in the above examples.

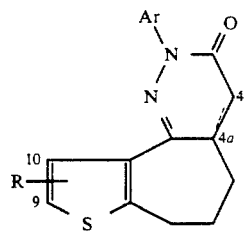

| No. | R | Ar | 4-4a bond |
|---|---|---|---|
| 13 | 9-CH$_3$ | 3-chlorophenyl | S |
| 14 | 9-CH$_3$ | 3-chlorophenyl | D |
| 15 | 9-CH$_3$ | 2-chlorophenyl | S |
| 16 | 9-CH$_3$ | 2-chlorophenyl | D |
| 17 | 9-CH$_3$ | 2-pyridyl | S |
| 18 | 9-CH$_3$ | 2-pyridyl | D |
| 19 | 9-CH$_3$ | 4-bromophenyl | S |
| 20 | 9-CH$_3$ | 4-bromophenyl | D |
| 21 | 9-CH$_3$ | 4-nitrophenyl | S |
| 22 | 9-CH$_3$ | 4-nitrophenyl | D |

-continued

[Structure: Ar-N-N=C fused to thiophene-cycloheptane ring system with carbonyl, positions 4, 4a, 9, 10 labeled, R substituent]

| No. | R | Ar | 4-4a bond |
|---|---|---|---|
| 23 | 9-CH$_3$ | 4-NH$_2$-C$_6$H$_4$- | S |
| 24 | 9-CH$_3$ | 4-NH$_2$-C$_6$H$_4$- | D |
| 25 | 9-CH$_3$ | 4-NHCOCH$_3$-C$_6$H$_4$- | S |
| 26 | 9-CH$_3$ | 4-NHCOCH$_3$-C$_6$H$_4$- | D |
| 27 | 9-CH$_3$ | 4-OH-C$_6$H$_4$- | S |
| 28 | 9-CH$_3$ | 4-OH-C$_6$H$_4$- | D |
| 29 | H | C$_6$H$_5$- | S |
| 30 | H | C$_6$H$_5$- | D |
| 31 | H | 4-Cl-C$_6$H$_4$- | D |
| 32 | H | 3-Cl-C$_6$H$_4$- | S |
| 33 | H | 3-Cl-C$_6$H$_4$- | D |
| 34 | H | 2-Cl-C$_6$H$_4$- | S |
| 35 | H | 2-Cl-C$_6$H$_4$- | D |
| 36 | H | 4-CH$_3$-C$_6$H$_4$- | D |
| 37 | H | 4-OCH$_3$-C$_6$H$_4$- | D |
| 38 | H | 2-pyridyl | S |
| 39 | H | 2-pyridyl | D |
| 40 | H | 4-Br-C$_6$H$_4$- | S |
| 41 | H | 4-Br-C$_6$H$_4$- | D |
| 42 | H | 4-NO$_2$-C$_6$H$_4$- | S |
| 43 | H | 4-NO$_2$-C$_6$H$_4$- | D |
| 44 | H | 4-CF$_3$-C$_6$H$_4$- | S |

-continued

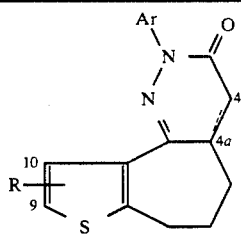

| No. | R | Ar | 4-4a bond |
|---|---|---|---|
| 45 | H | 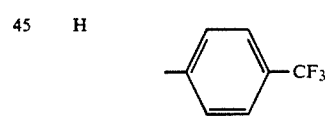 | D |
| 46 | H | 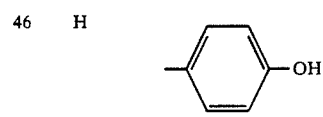 | S |
| 47 | H | 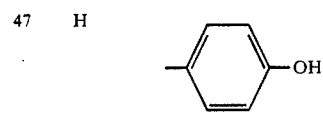 | D |
| 48 | 9-Br | 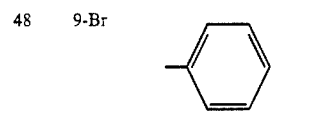 | S |
| 49 | 9-Br | 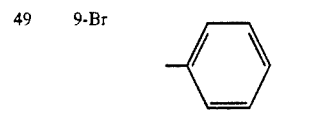 | D |
| 50 | 9-Br | 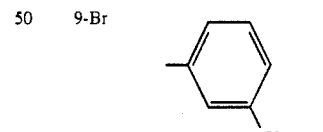 | S |
| 51 | 9-Br | 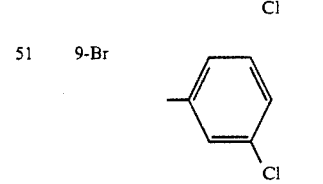 | D |
| 52 | 9-Br | 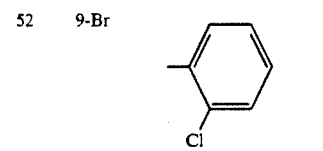 | S |
| 53 | 9-Br | 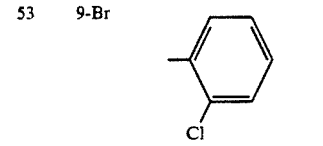 | D |
| 54 | 9-Br | 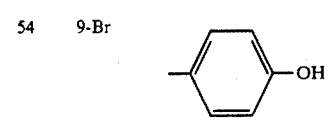 | S |

-continued

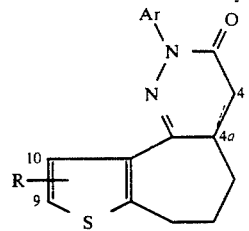

| No. | R | Ar | 4-4a bond |
|---|---|---|---|
| 55 | 9-Br | 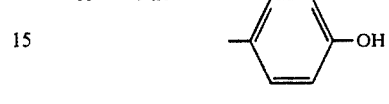 | D |
| 56 | 9-Br | 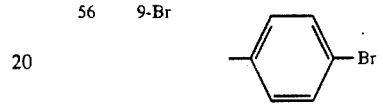 | S |
| 57 | 9-Br | 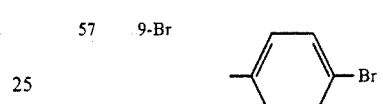 | D |
| 58 | 9-Br | 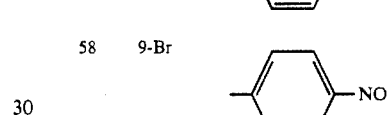 | S |
| 59 | 9-Br | 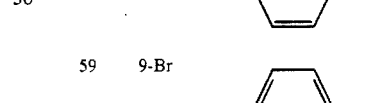 | D |
| 60 | 9-Br | 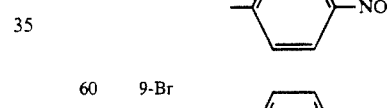 | S |
| 61 | 9-Br |  | D |

S: single bond, D: double bond

FORMULATION EXAMPLE

Tablets containing 10 mg of a compound of the formula (I) are prepared in accordance with the following formulation.

| | |
|---|---|
| Compound of formula (I) | 10.0 mg |
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound of the formula (I) is pulverized by an atomizer into fine powders below 10μ in average particle diameter, which are admixed with lactose, corn starch and crystalline cellulose sufficiently in a kneading machine, and further kneaded with polyvinylpyrrolidone paste. The kneaded mixture is passed through a sieve of 200 mesh, dried at 50° C. and passed through a sieve of 24 mesh. Talc and magnesium stearate are mixed therewith and the mixture is compressed into 120.0 mg tablets with a punch of 8 mm in diameter. These tablets are, if desired, subjected to sugar-coating or film-coating.

While the present invention has been adequately and sufficiently described in the foregoing specification including examples, the description can be changed or modified within the spirit and scope of this invention.

We claim:

1. A thienocycloheptapyridazine compound of the formula

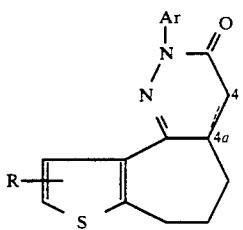

wherein R is hydrogen, halogen or $C_{1-4}$ alkyl; Ar is a member selected from the group consisting of phenyl, naphthyl, pyridyl, thienyl, pyrazolyl, imidazolyl, pyrimidinyl, pyridazinyl and benzimidazolyl, which Ar is unsubstituted or substituted by a member selected from the group consisting of halogen, $C_{1-4}$ alkyl, $C_{1-4}$ alkoxy, nitro, amino, hydroxy, trifluoromethyl and $C_{2-5}$ alkanoylamino; and the bond _____ between the 4-position and 4a-position is a single bond or a double bond.

2. A compound as claimed in claim 1 which is selected from the group consisting of 2-(4-chlorophenyl)-9-methyl-2,4,4a,5,6,7-hexahydro-3H-thieno[2',3':6,7]cyclohepta[1,2-c]pyridazin-3-one, 2-(4-methylphenyl)-9-methyl-2,4,4a,5,6,7-hexahydro-3H-thieno[2',3':6,7]cyclohepta[1,2-c]pyridazin-3-one, 2-phenyl-9-methyl-2,4,4a,5,6,7-hexahydro-3H-thieno-[2',3':6,7]cyclohepta[1,2-c]pyridazin-3-one, 2-(4-methoxyphenyl)-9-methyl-2,4,4a,5,6,7-hexahydro-3H-thieno-[2',3':6,7]cyclohepta[1,2-c]pyridazin-3-one, 2-(4-chlorophenyl)-2,5,6,7-tetrahydro-9-methyl-3-H-thieno-[2',3':6,7]cyclohepta[1,2-c]pyridazin-3-one, 2-(4-chlorophenyl)-2,4,4a,5,6,7-hexahydro-3H-thieno[2',3':6,7]-cyclohepta[1,2-c]pyridazin-3-one, 2-(6-chloro-2-pyridyl)-2,4,4a,5,6,7-hexahydro-3H-thieno[2',3':6,7]cyclohepta-[1,2-c]pyridazin-3-one, 2-(4-methylphenyl)-2,4,4a,5,6,7-hexahydro-3H-thieno[2',3':6,7]cyclohepta[1,2-pyridazin-3-one, 2-(4-methoxyphenyl)-2,4,4a,5,6,7-hexahydro-3H-thieno-[2',3':6,7]cyclohepta[1,2-c]pyridazin-3-one, 9-bromo-2-(4-chlorophenyl)-2,4,4a,5,6,7-hexahydro-3H-thieno[2',3':6,7]-cyclohepta[1,2-c]pyridazin-3-one, 9-bromo-2-(4-methoxyphenyl)-2,4,4a,5,6,7-hexahydro-3H-thieno[2',3':6,7]cyclohepta[1,2-c]pyridazin-3-one and 9-bromo-2-(4-chlorophenyl)-2,5,6,7-tetrahydro-3H-thieno[2',3':6,7]cyclohepta[1,2-c]pyridazin-3-one.

3. A pharmaceutical composition comprising a compound as claimed in claim 1 or 2 and a pharmaceutically acceptable additive.

4. A method of treating a patient having anxiety, which comprises administering to the patient an antianxiety effective amount of a compound as claimed in claim 1 or 2.

5. A method of treating a patient having amnesia, which comprises administering to the patient an antiamnesia effective amount of a compound as claimed in claim 1 or 2.

* * * * *